US006450995B1

(12) United States Patent
Prabhakar

(10) Patent No.: US 6,450,995 B1
(45) Date of Patent: Sep. 17, 2002

(54) DIAPER FOR AN INCONTINENT PERSON

(76) Inventor: Indira C. Prabhakar, 3175 Delevan Dr., Saginaw, MI (US) 48603

( * ) Notice: Subject to any disclaimer, the term of this patent is extended or adjusted under 35 U.S.C. 154(b) by 32 days.

(21) Appl. No.: 09/757,905

(22) Filed: Jan. 10, 2001

(51) Int. Cl.[7] .................................................. A61M 1/00
(52) U.S. Cl. ............................... 604/317; 604/385.101; 604/327
(58) Field of Search .................................. 604/317, 321, 604/318, 319, 320, 322–356, 183, 259, 393, 394; 4/144.1

(56) References Cited

U.S. PATENT DOCUMENTS

| | | | | |
|---|---|---|---|---|
| 3,757,356 A | * | 9/1973 | Freeman | 4/112 |
| 4,747,166 A | * | 5/1988 | Kuntz | 4/144 |
| 5,180,620 A | * | 1/1993 | Mende | 428/138 |
| 5,558,654 A | * | 9/1996 | Hardy | 604/322 |
| 5,584,826 A | * | 12/1996 | Faenger et al. | 604/322 |

* cited by examiner

*Primary Examiner*—Jeanette Chapman
(74) *Attorney, Agent, or Firm*—Reising, Ethington, Barnes, Kisselle, Learman & McCulloch, P.C.

(57) ABSTRACT

The suspended urinary external drainage system includes a liquid barrier with a periphery attached to a collector, with a tubular cross section, that encircles the barrier. A plurality of capillary tubes pass through a wall of the collector. Each of the plurality of capillary tubes has a capillary inlet adjacent to the liquid barrier and a capillary discharge inside the collector. A soft lining covers the capillary tubes. Discharge tubes connected to the collector carry urine to a holding bag.

12 Claims, 2 Drawing Sheets

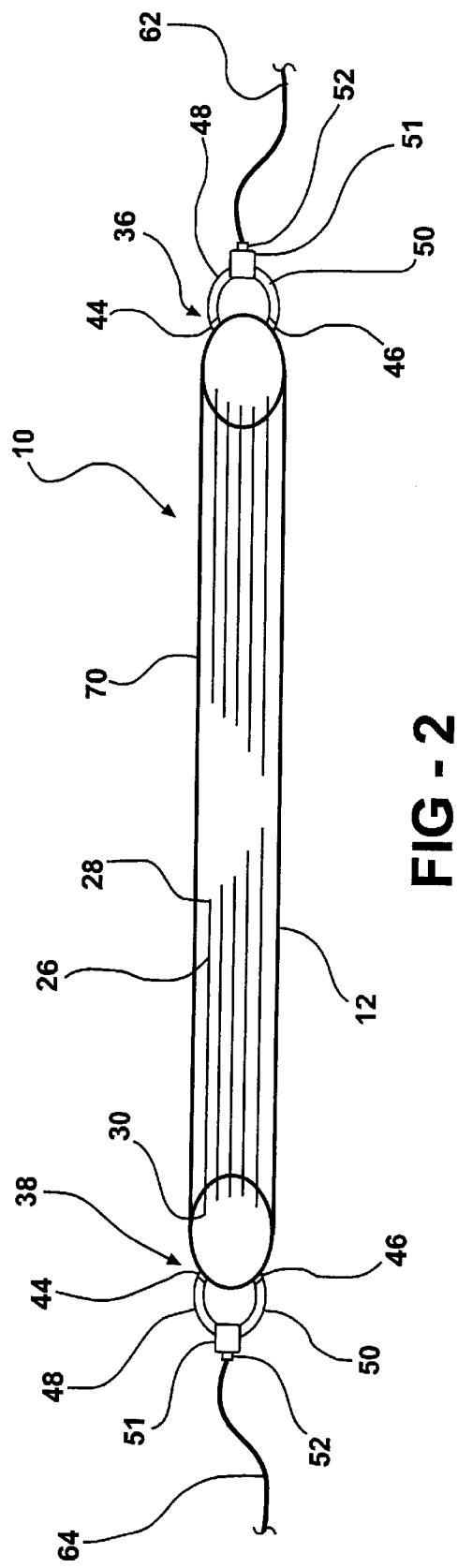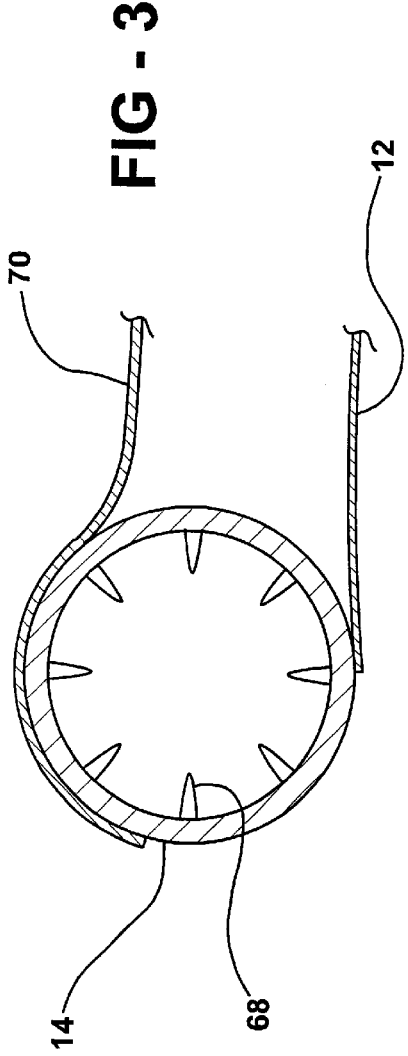

DIAPER FOR AN INCONTINENT PERSON

TECHNICAL FIELD

This invention relates to a suspended urinary external drainage system (SUEDS) for incontinent people and more particularly to a suspended urinary external drainage system type diaper which moves fluids from contact with a person's skin and delivers fluids to a holding bag.

BACKGROUND OF THE INVENTION

Cloth and paper diapers for small children work reasonably well. Children hold urine in their bladders for some period of time and then discharge a manageable quantity at one time. Periodic checks by parents or others generally result in diaper changes before skin problems develop due to prolonged exposure to urine. By the time a baby reaches the normal age for potty training, the quantity of urine discharged from the bladder at one time has increased. Conventional diapers have a limited capacity to hold liquids and may be overloaded at times when babies grow and become mobile. Problems with rashes and infections increase with age but are still manageable with adequate care.

Incontinent adults tend to discharge urine almost constantly. Cloth and paper diapers, worn by incontinent adults, are wet most of the time. Diapers worn by such adults must be changed frequently and even then skin problems occur. To reduce these problems with skin rashes and infections due to over exposure to urine, catheters have been developed. Female catheters are indwelling, tend to leak, become unattached, and frequently cause infections. For many females, catheters are unacceptable. Condom catheters for males are more successful but still have problems. They frequently fall off. Skin inside the condom is in contact with urine almost constantly and develops rashes which are difficult to treat.

Urethral catheters for males that are inserted into the urethra are superior to other catheters. They eliminate contact between the skin and urine. Skin rashes are substantially eliminated. Infections are not eliminated however. Catheter tubes must be removed frequently and replaced with clean tubes. Insertion of catheters into the urethra can be difficult and time consuming and is never a pleasant task. Infections that start in the urethra can spread to the bladder and kidneys. Kidney and bladder infections tend to be difficult to treat and can be fatal.

Individuals who are incontinent are generally older individuals. Most of them have other health problems and many are in medical facilities such as nursing homes. These individuals may require several man-hours of care daily. Providing such care is expensive.

Infections, that frequently afflict individuals that are incontinent, are treatable if the individual is otherwise healthy. Unfortunately, as mentioned above, incontinent individuals often have other medical problems. These other problems can make infections in the urinary tract more difficult to treat as stated above and may result in such infections becoming life threatening. A bladder or kidney infection can be fatal to a person with an artificial heart valve for example.

SUMMARY OF THE INVENTION

An object of the invention is to provide a suspended urinary external drainage system type diaper which drains urine away from exposed skin. Another object of the invention is to provide a diaper which catches urine that is drained away from the skin and is collects the urine in a collector. A further object of the invention is to drain urine from the collector into a holding bag. A still further object of the invention is to provide a diaper which remains comfortable and relatively dry for several hours when worn by an incontinent person. A yet still further object of the invention is to provide a relatively inexpensive extended wear diaper.

The diaper includes a substantial number of short capillary tubes positioned to receive urine and carry the urine to a collector. The collector is a ring-shaped member with a wall that the capillary tubes pass through. A liquid tight seal is formed between the capillary tubes and the wall of the collector. Drainage tubes are connected to the collector in positions in which at least one drainage tube will drain liquid from the collector when the person wearing the diaper is sitting, lying on the back, lying on the stomach or lying on a side. The discharge ends of the capillary tubes are near the center of the collector passage to ensure that fluids are not carried out of the collector by the capillary tubes.

The drainage tubes include one-way valves that prevent the flow of fluid from the drainage tubes into the collector. These one-way valves can be located in the drainage tube entries or between the drainage tube entries and the holding bag.

A pressure increase at the normal discharge end of the capillary tubes relative to the inlet end of the capillary tubes could prevent the flow of fluid into the capillaries and into the collector. A vent valve may be provided in the collector that equalizes the pressure of air inside the collector with the pressure of air outside of the collector. If necessary a tube can be connected to the vent valve to move the gas discharge away from the person wearing the diaper.

BRIEF DESCRIPTION OF THE DRAWINGS

The presently preferred embodiment of the invention is disclosed in the following description and in the accompanying drawings, wherein:

FIG. 2 is a sectional view taken along line 2—2 in FIG. 1; and

FIG. 3 is an enlarged sectional view taken along line 3—3 in FIG. 1.

DESCRIPTION OF THE PREFERRED EMBODIMENT

Figure 1:
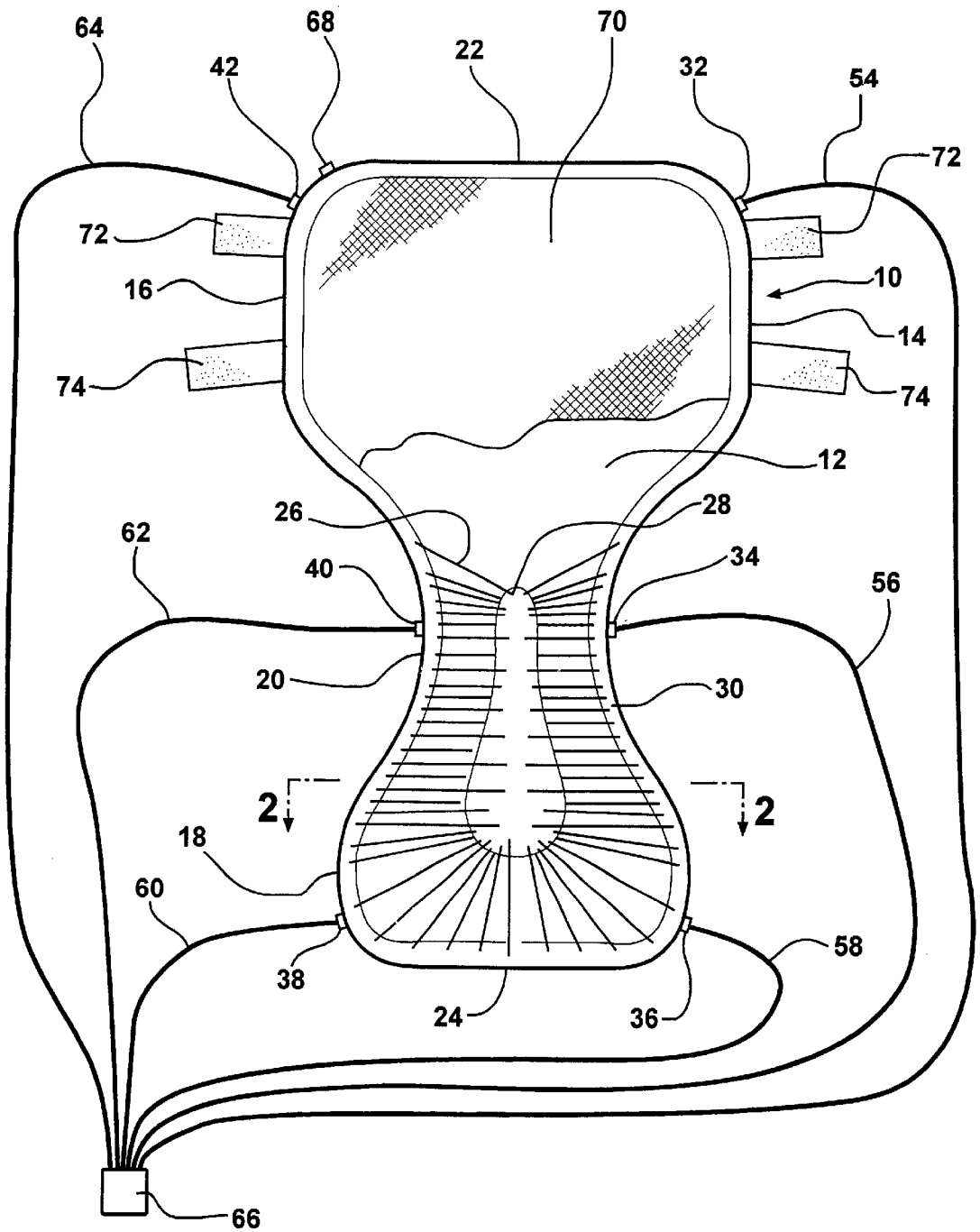
FIG. 1 is a top plan view of a diaper unfolded and laying in a generally flat plane with part broken away to shown the interior construction of the diaper.

The suspended urinary external drainage system type diaper 10 as shown in FIG. 10 has a flexible outer liquid barrier 12 made from a plastic material, a treated nylon material or other suitable material. The barrier 12 is connected to the collector 14. The collector 14 has a tubular cross section and preferably forms a ring that encircles the entire diaper 10. A flexible material is used to construct the collector. However, the collector 14 must maintain a central passage that permits the flow of liquid when such flow is required. The flow of liquid can be ensured by using a semi-rigid material for collector construction or by providing internal projections 68, shown in FIG. 3, that prevent the collector walls from collapsing.

The diaper 10 has a back half 16 and a front half 18 connected by crotch portion 20. The barrier 12 is narrow in the crotch portion 20 so that the barrier and two portion of the collector 14 can pass between the legs of a person wearing the diaper 10. The collector 14 as shown in FIG. 1 extends across the top portion 22 of the back half 16 as well as the top portion 24 of the front half 18. The portions of the collector 14 that extend across the top portion 22 of the back half 16 could be eliminated but in some situations fluid might be retained in the collector that should be discharged.

A large number-of capillary tubes 26 pass through the walls of the collector 14 and extend into the center section of the front half 18 of the diaper 10. Each capillary tube 26 has an inlet end 28 and a discharge end 30. The inlet ends 28 are positioned in a center portion of the front half 18 and in the crotch portion 20 where a plurality of the inlets can receive any fluids that are discharged and carry these fluids to the collector 14 under the force of gravity regardless of the position the person wearing the diaper 10 is in. The discharge ends 30 of the capillary tubes 26 are positioned away from the walls of the collector 14 so that any discharge fluids in the collector are generally out of contact with the discharge ends of other tubes. The capillary tubes 26 make sealing contact with the walls of collector 14 where they pass through the walls.

The capillary tubes 26 can be glass or plastic. If they are plastic, they must be a plastic that will not hold fluid droplets on their surfaces. Medical plastics used in heart pumps and blood filters can be used.

Discharge openings are provided at position 32 through 42 in the walls of the collector 14. Positions 32 and 42 are toward the top of the back half 16 of the diaper. Positions 34 and 40 are in the crotch area or portion 20. Positions 36 and 38 are near the top of the front half 18 of the diaper. At each position 32 through 42 there is preferably an upper opening 44 and a lower opening 46 as shown at positions 36 and 38 in FIG. 2. Two openings 44 and 46 are provided so that fluid can be drained from the collector 24 regardless of the position of the person wearing the diaper.

Each of the openings 44 is connected to a short discharge tube 48. Each opening,46 is also connected to is a short discharge tube 50. Each pair of short discharge tubes 48 and 50 are connected to a common T coupler 51 with an outlet 52. The short discharge tubes 48 and 50 have sufficient length for the outlet 52 to fall below the opening 44 and 46 depending on the orientation of the diaper 10.

Long discharge tubes 54, 56, 58, 60, 62, and 64 connect the out lets, 52 of each T coupler 51 to a holding bag 66. A one-way valve (not shown) is built into each T coupler 51 if desired to prevent the return flow of discharged fluids to the collector 14. If desired the long discharge tubes 54–64 can be connected to a common connector and a single final discharge tube can extend to the holding bag 66.

Long discharge tubes could also be connected directly to each of the openings 44 and the holding bag 66. Long discharge tubes would also have to be connected to the openings 46 and to the holding bag 66.

The capillary tubes 26 are covered with a fabric lining 70. The outer edge of the lining 70 is secured to the collector 14. This fabric lining 70 is a soft cotton material which permits urine to pass through to the inlet ends 28 of the capillary tubes 26. The cotton material is treated to prevent the absorption of liquid and keep the lining substantially dry.

Tape strips 72 and 74 on each side of the back half 16 of the diaper 10 can adhere to the front half 18 to hold the diaper on an individual.

The diaper 10 is made primarily from inexpensive synthetic materials. This makes it inexpensive to change the diaper 10 two or three times a day and keep the wearer dry substantially all the time. Skin problems are substantially reduced and infections are substantially eliminated. Labor costs are substantially reduced. Overall there will be significant savings.

The drain tubes 48 and 50 are removed from the collector 14 when the diaper 10 is changed. A disinfectant can be quickly forced through the drain tubes if desired. The holding bag 66 is discarded together with the urine collected and the disinfectant periodically.

The disclosed embodiment is representative of a presently preferred form of the invention, but is intended to be illustrative rather than definitive thereof. The invention is defined in the claims.

I claim:

1. A diaper comprising:
    a liquid barrier having a front area, a crotch area, a back area and a periphery;
    a lining, that permits the passage of liquid, secured to the periphery of the liquid barrier;
    a first plurality of capillary tubes, each of which has a first capillary tube inlet positioned between the front area of the liquid barrier and the lining and a first capillary tube discharge inside a collector;
    a second plurality of capillary tubes, each of which has a second capillary tube inlet positioned between the crotch area and the liquid barrier and the lining and a second capillary tube discharge inside the collector;
    and a seal between a collector wall of the collector and each of the plurality of first and second capillary tubes.

2. A diaper, as set forth in claim 1, wherein the first capillary tube discharge, of each of the plurality of capillary tubes, is spaced from a collector wall inside surface; and wherein the second capillary tube discharge, of each of the plurality of second capillary tubes is spaced from the collector wall inside surface.

3. A diaper, as set forth in claim 1, wherein the collector is secured to said barrier.

4. A diaper, as set forth in claim 1, wherein the collector has a plurality of collector discharge openings.

5. A diaper, as set forth in claim 4, wherein each of the plurality of collector discharge openings is connected to a liquid holding bag by a discharge tube.

6. A suspended urinary external drainage system comprising:
    a flexible outer liquid barrier material having a back portion, a front portion, a crotch portion that is integral with the back portion and the front portion, and an outer edge;
    a collector tube having a collector tube wall secured to an outer edge of the flexible outer liquid barrier and extending along a left side of the back portion, a left side of the crotch portion, a left side of the front portion, a front top side of the front portion, a right side of the front portion, a right side of the crotch portion and a right side of the back portion;
    a plurality of capillary tubes that pass through the collector tube wall and wherein each capillary tube in a first group of the plurality of capillary tubes has a first group inlet end positioned adjacent to a front portion inside surface of the flexible outer liquid barrier material, each capillary tube in a second group of the plurality of capillary tubes has a second group inlet end positioned adjacent to a crotch portion inside surface and the plurality of capillary tubes each have a discharge end inside the collector tube;
    a lining having a lining edge that is secured to the collector tube wall and wherein the lining permits the passage of liquid;

a plurality of liquid discharge openings through the collector tube wall; and discharge tubes connected to the liquid discharge openings.

7. A suspended urinary external drainage system as set forth in claim 6 wherein said collector tube is an endless ring that encircles the flexible outer liquid barrier material and wherein said collector tube extends along a rear topside of the back portion.

8. A suspended urinary external drainage system as set forth in claim 6 wherein the discharge end of each of the capillary tubes extends inward into said collector tube a distance past an inside surface of said collector tube.

9. A suspended urinary external drainage system as set forth in claim 6 wherein a seal is created between the wall of said collector tube and each of the plurality of capillary tubes.

10. A suspended urinary external drainage system as set forth in claim 9 wherein the discharge end of each of the plurality of capillary tubes is spaced from the seal between the wall of said collector tube and each of the plurality of capillary tubes.

11. A suspended urinary external drainage system as set forth in claim 6 wherein the lining is a soft non-absorbent material.

12. A method of collecting urine from an incontinent person comprising:

attaching a diaper with a liquid barrier and a lining to the incontinent person;

collecting urine that passes through the lining with a plurality of capillary tubes;

moving urine through the plurality of capillary tubes to a discharge end of each of the plurality of capillary tubes;

collecting urine discharged from the plurality of capillary tubes in a collector; and transferring urine from the collector to a urine holder.

\* \* \* \* \*